United States Patent

Hedberg et al.

Patent Number: 6,078,835
Date of Patent: Jun. 20, 2000

[54] PACEMAKER WHEREIN EMISSION OF STIMULATION PULSES IS CONTROLLED DEPENDENT ON STRETCHING OF THE VENTRICULAR WALL

[75] Inventors: Sven-Erik Hedberg, Kungsängen; Karin Järverud, Sundbyberg; Kjell Norén, Solna; Staffan Bowald, Almunge, all of Sweden

[73] Assignee: Pacesetter AB, Järfälla, Sweden

[21] Appl. No.: 09/242,278

[22] PCT Filed: Jul. 4, 1997

[86] PCT No.: PCT/SE97/01239

§ 371 Date: Feb. 12, 1999

§ 102(e) Date: Feb. 12, 1999

[87] PCT Pub. No.: WO98/06454

PCT Pub. Date: Feb. 19, 1998

[30] Foreign Application Priority Data

Aug. 14, 1996 [SE] Sweden .................................. 9602979

[51] Int. Cl.[7] ..................................................... A61N 1/365
[52] U.S. Cl. ................................................................. 607/9
[58] Field of Search ........................................... 607/9, 23

[56] References Cited

U.S. PATENT DOCUMENTS

| | | | |
|---|---|---|---|
| 4,052,991 | 10/1977 | Zacouto | 607/23 |
| 4,719,921 | 1/1988 | Chirife | 607/23 |
| 4,730,619 | 3/1988 | Koning et al. | 607/23 |
| 4,802,481 | 2/1989 | Schroeppel. | |
| 5,391,190 | 2/1995 | Pederson et al.. | |
| 5,417,715 | 5/1995 | Noren et al.. | |
| 5,496,361 | 3/1996 | Moberg et al.. | |
| 5,626,623 | 5/1997 | Kieval et al. | 607/23 |

FOREIGN PATENT DOCUMENTS

| | | |
|---|---|---|
| 0 288 630 | 11/1988 | European Pat. Off.. |
| WO 94/06513 | 3/1994 | WIPO. |
| WO 95/27531 | 10/1995 | WIPO. |

*Primary Examiner*—William E. Kamm
*Attorney, Agent, or Firm*—Hill & Simpson

[57] ABSTRACT

A pacemaker has control circuits contained in an enclosure and a lead containing an electrical conductor connected to an electrode for delivering electrical stimulation pulses to a heart. The stretching of a wall in the ventricle, corresponding to adequate filling of the ventricle in the heart, is determined in order to identify a time of emitting the stimulation pulses. This stretching is measured indirectly by measurement of pressure in the ventricle using a pressure sensor disposed near the lead in the ventricle. The signal from the sensor is supplied via the lead to circuitry in the enclosure, wherein the signal is amplified and is supplied to an edge detector, which detects an increasing or positive edge of the signal. The edge detector compares the incoming signal with a threshold value, and when the pressure indicated by the signal increases so as to exceed the threshold value, the edge detector supplies a signal to the control circuit which, in turn, triggers the emission of a stimulation pulse from a pulse generator, with or without a delay. The aforementioned stretching can also be measured using a strain gauge or a distance sensor attached to the ventricle wall.

9 Claims, 3 Drawing Sheets

PACEMAKER WHEREIN EMISSION OF STIMULATION PULSES IS CONTROLLED DEPENDENT ON STRETCHING OF THE VENTRICULAR WALL

BACKGROUND OF THE INVENTION

1. Field Of The Invention

The present invention relates to devices for determining the right time for delivering a stimulation pulse to a heart.

2. Description of the Prior Art

The ability to control heart rhythm with the aid of electrical stimulation is important to the well-being and survival of many people suffering from various heart defects. Battery-powered stimulation devices are available for different kinds of disorders, and they emit electrical impulses to trigger heart contractions, enabling the heart to perform its vital, blood-pumping function. The times at which stimulation pulses are delivered to a heart are determined in prior art automatic devices, in cases in which the heart retains at least partially normal electrical function, with the aid of some more or less easily measurable electrical unit, such as the chronological development of electrical voltage, in characteristic segments, measured between a stimulation electrode, or a separate sensor electrode, and the metal enclosure in which the stimulation device's battery and electrical control circuits are usually housed.

The electrical voltage developed by a heart has the following general pattern during a heart cycle. A low voltage pulse, the P wave, reflects electrical activity in the heart's atria when muscle cells in their walls contract. A more complex pulse segment is referred to as the QRS complex and comprises e.g. a large electrical pulse. This segment reflects electrical activity in the heart's ventricles when muscle cells contract in ventricular walls, thereby initiating and performing the heart's actual blood-pumping. Another low voltage pulse, indicating that cells in the ventricular walls are starting to recover from preceding contraction, is referred to as the T wave. These pulses/pulse segments normally follow each other in time, i.e. a P wave comes first in a heart cycle, followed by the QRS complex with the T wave last. However, if the QRS complex, for example, is absent or fails to appear at the right time, while a correct P wave is detected, the time at which a stimulation pulse is emitted for the purpose of triggering ventricular contraction and, accordingly, the heart's blood-pumping, can be determined from the time at which the P wave was detected.

An appropriately selected or advantageous time for emitting a stimulation pulse to trigger contraction of the heart's ventricles and ejection of blood for oxygenation and into the circulatory system can generally be regarded as the point at which sufficient blood has had time to flow into the ventricles so as to be pumped out. This can also be put another way, i.e. a stimulation pulse should be delivered as soon as the heart's ventricles contain sufficient blood. This makes the heart's blood-pumping effective and does not impose any needless mechanical strain on heart muscle, since this muscle only needs to remain in the stretched state for a brief period of time.

Determination of this appropriate time can be made from the electrical impedance measured between a stimulation electrode in a ventricle and some other electrode in the body or in the heart. This impedance is related, in a complex way, to the amount of blood in the ventricle, a circumstance utilized in U.S. Pat. No. 5,417,715, which is attached here as, and can be used for detecting the degree to which the ventricle of the heart is full. Thus, this patent depicts heart stimulation at a variable stimulation interval, the time for emitting a stimulation pulse being governed by the impedance, measured between an end electrode and a ring electrode, both of which installed in the same ventricle. The minimum of the curve of the impedance tracing is identified, and a stimulation pulse is emitted, after a pre-defined delay, when the curve subsequently increases to a given percentage of the aforementioned minimum. One disadvantage of this method is that correspondence between impedance and the degree of filling is not always unequivocal due to the fact that impedance measurements primarily reflect conditions close to the measurement site, e.g. around the electrode tip.

SUMMARY OF THE INVENTION

One object of the invention is to provide a device for determining suitable times for the emission of stimulation pulses related, in a relatively direct manner, to a heart ventricle's degree of filling.

The problem solved by the invention is to avoid shortcomings in measurement of impedance to designate the degree of blood filling and finding, in a more direct fashion using other devices, a suitable time for the emission of stimulation pulses to a heart, its ventricles in particular.

It is known that the magnitude of peripheral resistance to blood pumped out of a person's heart is a function of the exercise performed by the person. The greater the intensity of that exercise, the less the peripheral resistance. Therefore peripheral resistance is a good measure of exercise performed. The less the resistance, the faster the filling of the heart's right ventricle. According to the above, a suitable time for delivering a stimulation pulse to the heart is when the ventricle has filled with sufficient blood.

When the ventricle fills with blood, muscle cells in the wall of the ventricle stretch, i.e. their length increases to an appropriate tension, so an appropriate time for stimulation can therefore be set as the time at which the muscle cells have stretched to an appropriate degree. This stretching can be measured or determined in a more or less direct manner, and the time for a stimulation pulse can be made dependent on the time at which a measurement value, representing the heart wall, S degree of stretching during a phase in which stretching increases, achieves some appropriate threshold value.

The heart wall's stretching can be measured directly with a sensor attached to the heart wall, e.g. on the exterior of same. The sensor for measuring stretching can be some kind of distance sensor, such as a differential transformer, attached to the heart wall at two separate points. Alternately, stretching can be measured indirectly by measurement of pressure in the ventricle with a pressure sensor located in the ventricle, e.g. on the electrode used for stimulating the ventricle.

DESCRIPTION OF THE PREFERRED EMBODIMENTS

Figure 1:
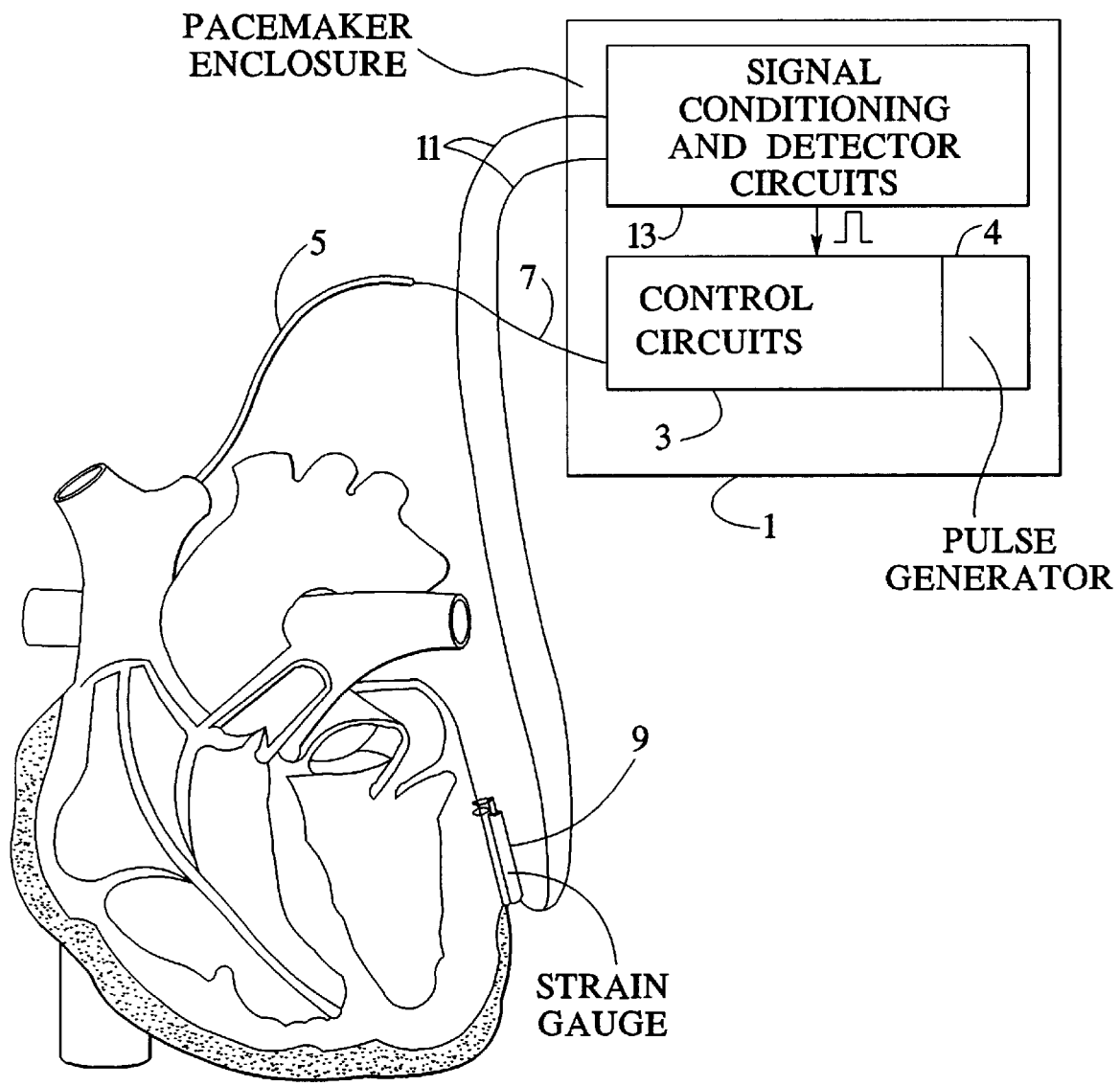
FIG. 1 schematically depicts a stimulation device with measurement of a heart wall's degree of stretching.

As initially discussed, a suitable time for delivering a stimulation pulse to a ventricle of the heart is when the ventricle has filled with sufficient blood. Here, "sufficient" can be regarded as being when enough blood has entered to achieve optimal pumping of blood without the need for excessive stretching of muscle cells in the heart wall. If the time is selected well, mechanical and physiological strain on the heart muscle can be made as small as possible with a view to the general physiological condition of the patient to whom the heart belongs. As blood flows in, stretching of muscle cells can be detected by a strain gauge, a device for measuring elastic, linear deformation, attached to the heart wall, and a heart stimulation device or pacemaker utilizing same is schematically depicted in FIG. 1.

The pacemaker's electronic control and source of energy are enclosed in a shell or capsule, schematically suggested at 1. An electrode lead 5 runs from control circuits 3, encompassing a pulse generator 4 in the enclosure 1, to the lower apex of the right ventricle of a person's heart. The lead 5 contains an insulated electrical conductor 7 for a stimulation electrode (shown only generally, not in detail) arranged in the usual manner on the distal, free end of the lead 5. A mechanical strain gauge 9 is arranged on the exterior of the heart wall, i.e. on the exterior of the heart's left ventricle in the FIG. Two electrical conductors 11 pass from this sensor 9 to electronic signal conditioning and detector circuits 13, arranged inside the enclosure 1, which send electrical pulses at appropriate times, according to the detected stretching, to the pacemaker's control circuits 3. Many types of strain gauges can be used as the sensor 9, e.g. a movement sensor such as a differential transformer of the known kind. Different parts of the sensor must be attached at two separate points on the heart wall in order to emit an electrical signal designating the distance between these two points. The signal is conditioned in the conditioning and detector circuits 13 so it is e.g. largely proportional to the distance between the sensor's attachment points and, accordingly, to the heart wall's degree of stretching. The conditioned signal is then processed by a detector circuit, arranged, when detecting a signal, to send a control signal to the pacemaker's control circuits 3 if the detected signal is increasing and exceeds or reaches a threshold level. This threshold must be set at an appropriate level so the control circuits emit a stimulation pulse when stretching corresponds to optimal blood-filling. The choice of a threshold level is further discussed below in conjunction with the description of another embodiment of the stimulator. The control circuits 3 emit stimulation pulses, via the pulse generator 4, over the conductor 7 at points derived in an appropriate manner, e.g. from the times, with some delay, at which they receive a pulse from the signal conditioning and detector circuits 13.

Figure 2:
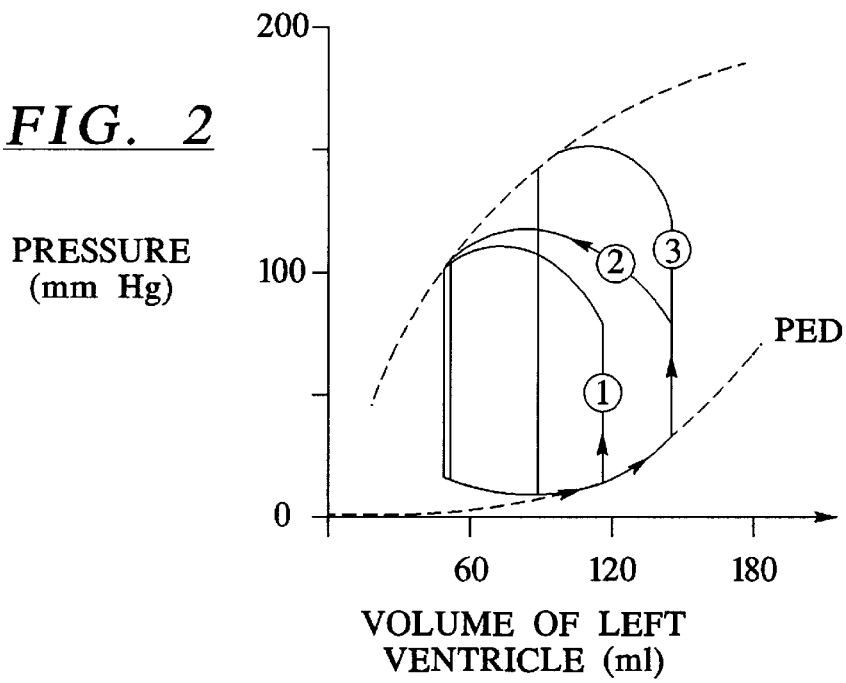
FIG. 2 is a diagram of pressure as a function of the volume of the left ventricle in heart cycles subjected to different degrees of loading.

Stretching of the heart ventricle wall can also be determined in a more indirect fashion which, however, is more "directly" related to stretching and, accordingly, the degree of blood-filling than electrical impedance measured between two electrodes in the ventricle. As a result of the ventricle's closed, curved shape, the hydrostatic pressure of blood in the ventricle is directly related to wall stretching, provided some simple relationship such as Hooke's Law is assumed to apply to the relationship between mechanical tension and the stretching of tissue in the walls. Such a relationship can be assumed to apply to the relaxed state of the muscle cells while filling is in progress after each pump stroke. At this stage, blood filling is also directly and unequivocally related to hydrostatic pressure, as shown in FIG. 2. It is a diagram of pressure in the left ventricle of the heart as a function of ventricular volume. The relationships in different heart cycles are depicted by the closed tracings at ①, ② and ③.

The interesting segments here will be found in the lower right part of the tracings where they coincide with the lower dashed tracing designated PED. When a stimulation pulse triggers contraction, the closed tracings rise straight reflecting a pressure increase, that occurs prior the pumping begin at the point at which the vertical flank changes to a curve denoting a declining volume and a continued increase in pressure.

Figure 3:
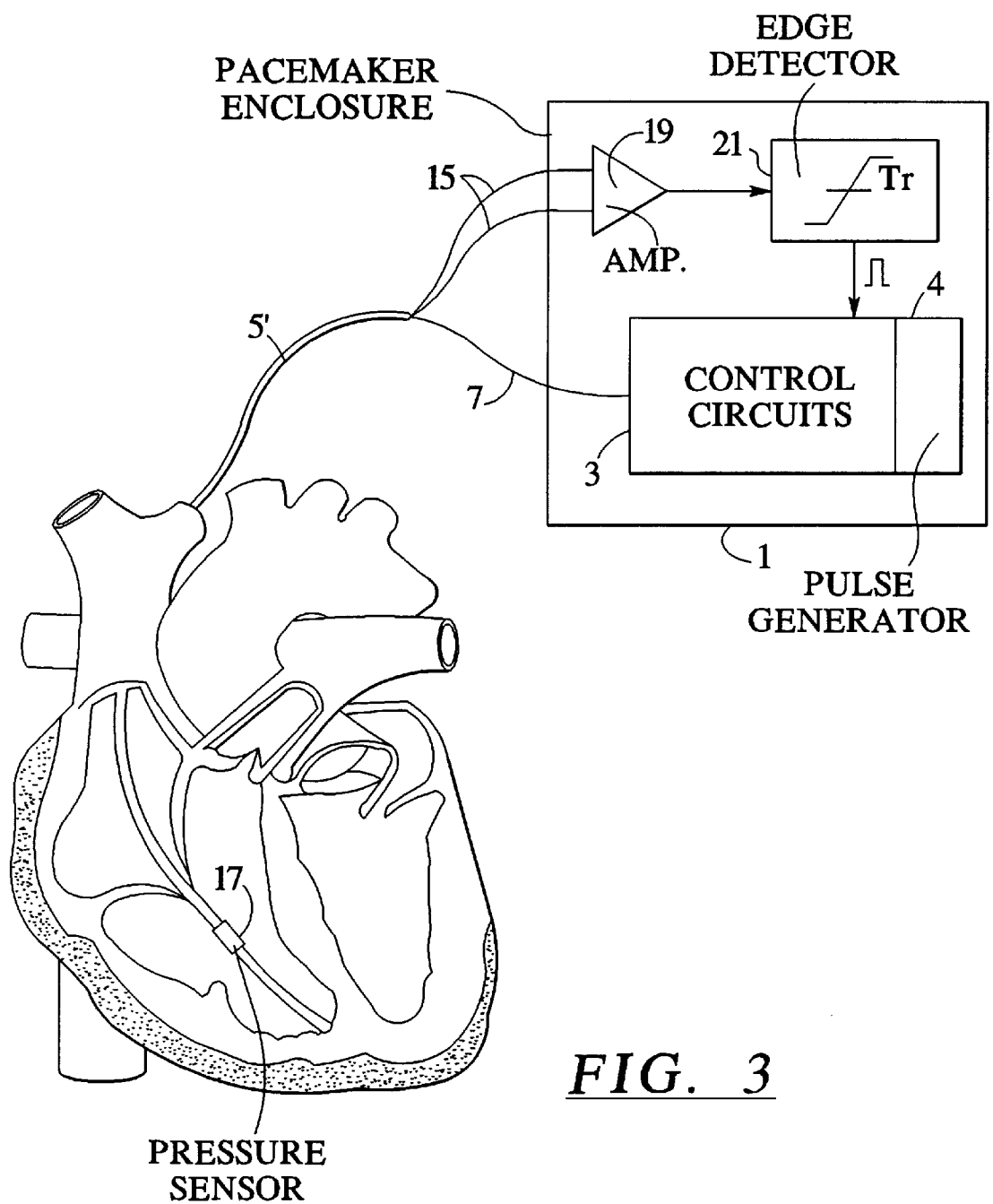
FIG. 3 schematically depicts a stimulation device with measurement of pressure in a heart ventricle.

The construction of a pacemaker utilizing a pressure sensor for emitting stimulation pulses at appropriate times is schematically shown in FIG. 3. As in the aforementioned embodiment, an electrode lead 5' extends from the pacemaker enclosure or main section 1 to the lower apex of the right ventricle of the heart. However, the lead 5' here contains a plurality of electrical conductors, insulated from each other and the surroundings, like the lead 5' above, and extending to a stimulation electrode (not shown but arranged e.g. on the end of the lead 5'). The lead 5 is connected to the pacemaker's electrical control circuits 3 which, as above, are located in the main part 3 and emits stimulation pulses, generated by the pulse generator 4, via this lead 5'.

The lead 5' also contains two other electrical conductors 15, which are electrically insulated from each other and from the conductor 7, and are connected to a pressure sensor 17 arranged on or by the lead 5'. The pressure sensor 17 is located at a slight distance from the free, outer end of the lead 5', placing it at a slight distance from the interior wall of the ventricle but still well-inside this ventricle. The pressure sensor 17 sends an electrical signal, representing the pressure of the medium which surrounds and acts on the sensor's 17 pressure-sensitive surface, via the conductors 15. The signal is sent to circuits inside the main section 1, first to an amplifier 19, which can also be equipped with appropriate filters, e.g. at least a high pass filter, depending on the type of pressure sensor and the way in which it is driven. The amplified and possibly filtered signal is sent to a positive edge or rising edge detector 21 which, in the same way as for strain gauges, emits a brief electrical pulse each time the signal at such a edge reaches and exceeds a carefully selected threshold value Tr.

This brief pulse is sent to the pacemaker control circuits 3 and a stimulation pulse is delivered via the conductor 7, from the pulse generator 4, to the heart. When a pulse from the detector circuit 21 reaches the control circuits 3, the emission of the stimulation pulse might be delayed by a predefined delay period, depending e.g. on the magnitude of the triggering level Tr set for the detector 15. The control circuits 3 can otherwise be equipped with various safety features so e.g. stimulation pulses are always emitted at some appropriate interval, even if no pulse is received from the detector circuit 21 within a predefined period of time after the preceding stimulation pulse.

Figure 4A:
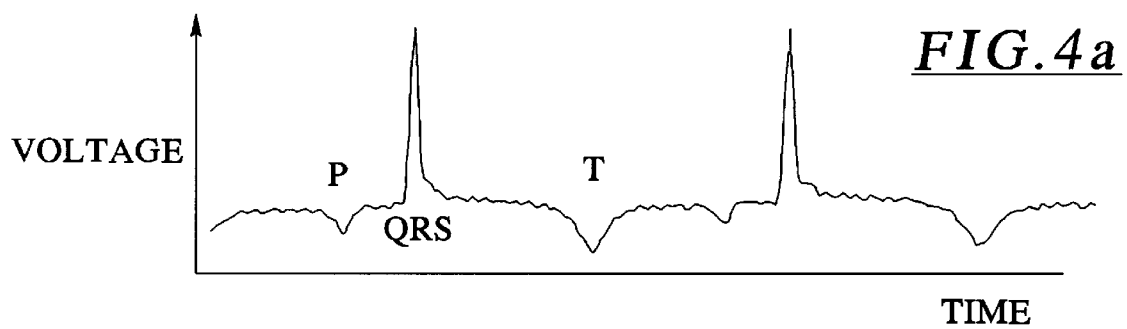
FIG. 4a shows a surface ECG.
Figure 4B:
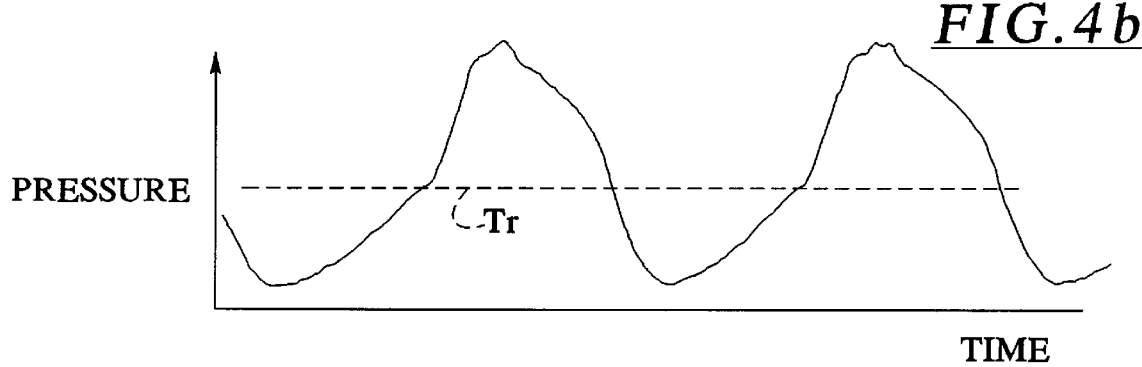
FIG. 4b is a diagram of pressure in a ventricle of the heart as a function of time.

In order to clarify the way in which the threshold level or triggering level Tr can be selected, FIGS. 4a and 4b contain diagrams of electric voltage and pressure respectively as a function of time. Thus, FIG. 4a is a diagram showing the electrical voltage sequence between two points on the body, the points being placed on opposite sides of a heart. This kind of recording is referred to as surface ECG, and its appearance is analogous to the course of events discussed initially regarding the voltage between one point on the heart and another, internal point in the body. Thus, the P wave, QRS complex and the T wave are distinguishable here and designate the various events described above.

FIG. 4b is a diagram showing pressure in the right ventricle of a healthy heart as a function of time. The time scales in FIGS. 4a and 4b agree with one other. As can be seen in FIG. 4b, pressure is lowest at a point somewhat after the T wave, i.e. somewhat after the time at which muscle cells in the walls of the ventricle start to relax and lengthen. Here, blood flows into the ventricle from the associated atrium, and pressure rises. At some point in the latter part of the QRS complex, pressure starts rising more rapidly. This indicates that the walls of the ventricle are contracting, and blood is being pumped out of the ventricle. Pressure rises to a peak value and then falls to a nadir value at a more or less uniform rate. The entire process is then repeated. An appropriately selected triggering level for the edge detector 15 is shown at Tr, selected so it lies at the point at which pressure begins rising more rapidly. This level can be established e.g. if the derivative of the pressure signal is studied and assigned an appropriate a value corresponding to the level at which the derivative of the pressure signal exceeds a predefined value. The pressure level can also be determined in other ways, e.g. by pattern recognition or measurement of absolute pressure. Another condition for the level could be that it simultaneously exceeds a predefined pressure.

In a heart with absent intrinsic ventricular stimulation, the time selected for stimulation will closely simulate chronologically natural ventricular function in pumping out blood.

In the customary manner, the control circuits 3 of both embodiments can contain various functions to ensure that stimulation pulses are generated at a specific slowest rate and fastest rate and that change in intervals between pulses cannot be made too rapidly. U.S. Pat. No. 5,417,715 cited above.

Although modifications and changes may be suggested by those skilled in the art, it is the intention of the inventors to embody within the patent warranted hereon all changes and modifications as reasonably and properly come within the scope of their contribution to the art.

We claim:

1. A pacemaker for delivering electrical stimulation pulses to a heart, with a ventricle exhibiting systole and diastole, of a subject, said subject experiencing a physiological load which produces physiological and mechanical strain on the heart, said pacemaker comprising:

an electrode lead;

a stimulation electrode connected to a free first end of said lead;

electrical control circuits including a pulse generator connected to a second, opposite end of said lead;

a sensor for measuring stretching of a wall of a ventricle of the heart and for emitting a first electrical signal at a level corresponding to the stretching of said wall;

a detector circuit having a threshold representing optimal blood-filling of the ventricle dependent on said physiological load and said physiological and mechanical strain, said detector circuit being connected to the sensor for receiving the first signal, and connected to the control circuits, and comparing said level of the first signal to said threshold and generating a second electrical signal during diastole if and when the level of the first signal is monotonically increasing and exceeds the threshold, said detector circuit supplying the second signal to the control circuits; and upon receipt of said second electrical signal, the control circuits emitting a control signal to said pulse generator causing the pulse generator to emit a stimulation pulse delivered to said heart via said electrode lead and said stimulation electrode.

2. The pacemaker according to claim 1, wherein the sensor comprises a pressure sensor adapted for placement in said ventricle of the heart.

3. The pacemaker according to claim 2, wherein the pressure sensor is mounted on the lead at a distance from said free first end.

4. The pacemaker according to claim 1, wherein the sensor comprises a strain gauge adapted for attachment to a wall of said ventricle of the heart.

5. A pacemaker according to claim 4, wherein said strain gauge is adapted for attachment to an exterior of said wall of said ventricle of the heart.

6. The pacemaker according to claim 1, wherein the sensor comprises a differential transformer adapted for attachment to a wall of said ventricle of the heart.

7. A pacemaker according to claim 6, wherein said strain gauge is adapted for attachment to an exterior of said wall of said ventricle of the heart.

8. The pacemaker according to claim 1, wherein said detector circuit comprises means for calculating a derivative of the first signal and for determining a level at which said derivative exceeds a predefined value, and means for setting the threshold is set in the detector circuits at said level at which a derivative of the first signal exceeds a predefined value.

9. A pacemaker according to claim 1, wherein said control circuits include a delay circuit for interposing a delay between receipt of said second electrical signal and emission of said control signal.

* * * * *